(12) United States Patent
Chan et al.

(10) Patent No.: US 9,086,410 B2
(45) Date of Patent: Jul. 21, 2015

(54) DOWNWARD OR VERTICAL FLOW DIAGNOSTIC DEVICE AND ASSAY

(75) Inventors: Hermes K. W. Chan, Halifax (CA); King Sing Chan, Hammonds Plains (CA); Neeraj Vats, Halifax (CA)

(73) Assignee: MEDMIRA INC., Halifax, Nova Scotia (CA)

( * ) Notice: Subject to any disclaimer, the term of this patent is extended or adjusted under 35 U.S.C. 154(b) by 967 days.

(21) Appl. No.: 13/124,758

(22) PCT Filed: Oct. 16, 2009

(86) PCT No.: PCT/CA2009/001468
§ 371 (c)(1),
(2), (4) Date: Jul. 1, 2011

(87) PCT Pub. No.: WO2010/043044
PCT Pub. Date: Apr. 22, 2010

(65) Prior Publication Data
US 2011/0256638 A1      Oct. 20, 2011

Related U.S. Application Data

(60) Provisional application No. 61/106,291, filed on Oct. 17, 2008.

(51) Int. Cl.
G01N 33/543     (2006.01)

(52) U.S. Cl.
CPC .............................. *G01N 33/54386* (2013.01)

(58) Field of Classification Search
USPC ......... 422/401, 408, 411, 413, 414, 417, 420, 422/421, 425, 426; 435/288.4, 288.5
See application file for complete search history.

(56) References Cited

U.S. PATENT DOCUMENTS

| | | | |
|---|---|---|---|
| 3,888,629 | A | 6/1975 | Bagshawe |
| 4,632,901 | A | 12/1986 | Valkirs et al. |
| 4,818,677 | A | 4/1989 | Hay Kaufman |
| 4,943,522 | A | 7/1990 | Eisinger et al. |
| 5,006,464 | A | 4/1991 | Chu et al. |
| 5,160,701 | A | 11/1992 | Brown et al. |

(Continued)

FOREIGN PATENT DOCUMENTS

| | | |
|---|---|---|
| WO | 01/11374 | 2/2001 |
| WO | 2005/085855 | 9/2005 |
| WO | 2007/111651 | 10/2007 |

*Primary Examiner* — Chris L Chin
(74) *Attorney, Agent, or Firm* — Nixon Peabody LLP; David S. Resnik; Shayne Y. Huff (57) ABSTRACT

A downward or vertical flow-through rapid diagnostic device and assay are provided. The device comprises a test area and reagent storage area, which are linked via a channel. The test area further comprises a reaction zone and an absorbent zone. A capture reagent is immobilized on the reaction zone to detect a target analyte in the fluid test sample. The fluid test sample flows downward or vertically through the reaction zone and into the absorbent zone, with the capture reagent and target analyte forming a two-membered complex that is concentrated in the reaction zone. The reagent storage area comprises a breakable cartridge positioned directly and vertically above the test area and a channel. A reagent used in the assay is housed in the breakable cartridge. Once liberated, the reagent passes through the channel and flows to test area for depositing on the reaction zone. The storage of predetermined amounts of reagents in the diagnostic device reduces the number of manual operations required to produce a result.

15 Claims, 5 Drawing Sheets

(56) References Cited

U.S. PATENT DOCUMENTS

| | | |
|---|---|---|
| 5,185,127 A | 2/1993 | Vonk |
| 5,541,059 A | 7/1996 | Chu |
| 6,656,428 B1 * | 12/2003 | Clark et al. .................. 422/404 |
| 7,090,803 B1 * | 8/2006 | Gould et al. .................. 422/413 |
| 7,531,362 B2 | 5/2009 | Chan |
| 7,638,093 B2 * | 12/2009 | Wang et al. .................. 422/417 |
| 2003/0049857 A1 | 3/2003 | Chan |
| 2007/0190667 A1 | 8/2007 | Cole et al. |

\* cited by examiner

DOWNWARD OR VERTICAL FLOW DIAGNOSTIC DEVICE AND ASSAY

CROSS-REFERENCE TO RELATED APPLICATIONS

This application is a U.S. national stage application of International Application No. PCT/CA2009/001468 filed on Oct. 16, 2009, which claims the benefit of priority of U.S. Provisional Application No. 61/106,291 filed on Oct. 17, 2008, both of these applications being incorporated herein their entireties by reference.

FIELD OF THE INVENTION

The present invention generally relates to a diagnostic device and assay for the detection of a target analyte in a fluid test sample. More specifically, the present invention relates to a downward or vertical flow diagnostic device having the reagents used in the assay contained within the device.

BACKGROUND OF THE INVENTION

Point of Care Tests have become increasingly common over the past several years. These tests are simple to perform, require little or no extra equipment, and typically produce results in a relatively short period of time compared to traditional laboratory tests. There are primarily two technological platforms available in the Point of Care test market: lateral flow and flow-through, each of which can be used for many applications.

While both lateral flow and flow-through test devices utilize the same biological principles, namely detection of target analytes such as antibodies or antigens in a bodily fluid, they differ in their methods for detecting antibody-antigen complexes.

For example, Eisinger et al., U.S. Pat. No. 4,943,522, describes a lateral flow diagnostic device in which the test sample is applied to one end of the device and then transferred laterally across a membrane to be visualized in one or more indicator zones.

A common problem with most lateral flow devices is that the amount of time required to transfer the test sample laterally from the sample application zone to the indicator zones may not be ideal for certain time sensitive applications, such as emergency departments, labour and delivery settings and needle stick injuries.

Accordingly, flow-through devices offer advantages over lateral flow devices in that they are often more compact and can provide more rapid results. Examples of such flow-through devices can be found in Brown et al., U.S. Pat. No. 5,160,701 and Chan, U.S. Pat. No. 7,531,362.

Brown et al., USP '701 describe a flow-through device in which the fluid test sample is applied to a reaction matrix containing a capture reagent bound to the matrix that is capable of binding to a target analyte in the test sample. The remaining portion of the test sample flows through the reaction matrix into an absorbent pad. After several rounds of washing, the presence or absence of the target analyte in the fluid test sample is visually determined following the manual addition of a liquid indicator reagent. The Brown et al., device requires the manual addition of several buffers and reagents in order to achieve a result. These manual steps not only increase the amount of time required to complete an assay, but also increase the potential for error in the assay. In addition, some of reagents required for use with the Brown et al., device require refrigeration or have to be prepared immediately prior to use in the assay, thus limiting the environments in which the device can be used.

Chan, USP '362, provides a flow-through device that eliminates several of the washing steps required by Brown et al., thus decreasing the overall time required to successfully complete an assay. Furthermore, Chan provides a post-filter unit containing a dried indicator reagent that is applied to the test device after the test sample has permeated through the reaction matrix. A buffer is applied to the post-filter unit to resolubilize the indicator reagent. The resolubilized indicator reagent is then able to interact with the two-membered complex formed in the reaction zone between the target analyte and the capture reagent. By providing the indicator reagent in a dried format in a post-filter unit, the assay requires only a single buffer, fewer washing steps, and can be stored at room temperature.

Although the Chan device efficiently provides results in a timely manner, it would be desirable to have a rapid diagnostic device that improves the efficiency of the Chan device by further reducing the required number of manual additions of reagents and buffers than the traditional downward or vertical flow through devices.

SUMMARY OF THE INVENTION

It is an object of the present invention to provide a downward or vertical flow diagnostic device that requires less manual addition of reagents and buffers during operation and thus overcomes the limitations of the prior art.

It is a further object of the present invention to provide an assay that requires less reliance on the manual delivery of reagents and buffers to the assay, thus minimizing the potential for error.

According to an aspect of the present invention, there is provided a downward or vertical flow through test device for determining the presence or absence of a target analyte in a fluid test sample. The test device comprising: a test area and a reaction area. The test area comprises: a reaction zone to which the fluid test sample is applied so that the fluid test sample flows downwardly or vertically through the reaction zone, the reaction zone comprising an immobilized capture reagent that binds the target analyte in the deposited fluid test sample, and an absorbent zone in vertical communication with the reaction zone, the absorbent zone comprising an absorbent material positioned underneath the reaction zone for facilitating the downward or vertical flow of the fluid test sample through the reaction zone and into the absorbent zone. The reagent storage area comprising: at least one breakable cartridge housing a liquid reagent positioned directly and vertically above at least a portion of the test area, and a channel connecting the breakable cartridge to the test area, whereby liberating the liquid reagent from the breakable cartridge causes the reagent to flow vertically or downwardly through the channel onto the test area.

In one embodiment, a matrix having dried indicator reagent embedded therein is provided. The matrix being positioned between the breakable cartridge and the test area, whereby the liberated liquid reagent flows through the matrix to reconstitute the indicator reagent.

In another embodiment, an actuator for breaking the breakable cartridge is provided, wherein activating the actuator causes the breakable cartridge to break and release the liquid reagent therefrom.

In a further embodiment, a liquid permeable member is positioned to support the breakable cartridge allowing the liberated liquid reagent to flow downward or vertically through the liquid permeable member.

In yet a further embodiment, a second liquid permeable member positioned between the matrix and the test area. The second liquid permeable member can be positioned to support the matrix and functions to control the rate of flow of the liquid reagent containing the reconstituted indicator reagent from the matrix to the channel.

In an embodiment, two or more reagent storage areas are provided and each reagent storage area is connected to the test area via a dedicated channel. In another embodiment, the two or more reagent storage areas are provided and the reagent storage areas are connected to the test area via one or more common channels.

In a further embodiment, the reagent storage area is provided in a housing positioned on the test device. Alternatively, the reagent storage area is provided in a housing confined within the test device In another embodiment, more than one immobilized capture reagent is provided in the reaction zone.

A flexible membrane that allows for compression of the breakable cartridge can also be provided.

In an embodiment, a barrier surrounding the matrix to limit the lateral movement of the matrix within the reagent storage area.

In yet a further embodiment, the breakable cartridge is pressure fitted into a space defined by the housing to prevent lateral movement of the breakable cartridge within the housing.

In one embodiment, one or more vents positioned between the barrier and the housing to facilitate the movement of air within the housing.

In an embodiment, the liquid reagent is an indicator reagent capable of binding to a two-membered complex formed between the capture reagent and the target analyte.

In one embodiment, the reagent storage area is located directly above the test area such that reagent liberated from the reagent storage area flows downward through an aperture onto the test area, flooding the entire test area.

According to another aspect of the present invention, there is provided a method of determining the presence or absence of a target analyte in a fluid test sample. The method comprising the steps of: applying the fluid test sample to a reaction zone of a test unit, whereby the fluid test sample flows downwardly or vertically through the reaction zone, the reaction zone comprising an immobilized capture reagent that binds the target analyte in the deposited fluid test sample to form a two-membered complex of a specific binding interaction; allowing the fluid test sample to flow downwardly or vertically through the reaction zone into an absorbent zone in vertical communication with the reaction zone, the absorbent zone comprising an absorbent material positioned underneath the reaction zone for facilitating the downward or vertical flow of the fluid test sample through the reaction zone so as to concentrate the two-membered complex in the reaction zone; activating a breakable cartridge positioned directly and vertically above at least a portion of the test area to liberate a liquid reagent contained therein, transporting the liquid reagent through a channel to the reaction zone of the test area; allowing the liquid reagent to flow downwardly or vertically through the reaction zone and into the absorbent zone to bind with the two-membered complex concentrated in the reaction zone, with any unbound reactants being washed from the reaction zone; and observing a test result depicted by a presence or absence of a visually detectable signal on the reaction zone.

In one embodiment, the method further comprises the step of allowing the liberated reagent to flow through a liquid permeable member prior to being transported through the channel.

In another embodiment, the method further comprises the step of allowing the liberated reagent to flow through a matrix comprising a dried indicator reagent to resolubilize the indicator reagent prior to being transported through the channel.

In a further embodiment, the liquid reagent is an indicator reagent capable of binding to the two-membered complex.

According to another aspect of the present invention, there is provided a downward or vertical flow through test device for determining the presence or absence of a target analyte in a fluid test sample. The test device comprising a test area and a reagent storage area. The test area comprising: a reaction zone to which the fluid test sample is applied so that the fluid test sample flows downwardly or vertically through the reaction zone, the reaction zone containing an immobilized capture reagent that binds the target analyte in the deposited fluid test sample, and an absorbent zone in vertical communication with the reaction zone, the absorbent zone comprising an absorbent material positioned underneath the reaction zone for facilitating the downward or vertical flow of the fluid test sample through the reaction zone and into the absorbent zone. The reagent storage area comprises: at least one breakable cartridge housing a liquid reagent, and a liquid permeable member positioned between the breakable cartridge and the test area; and a channel connecting the reagent storage area to the test area for facilitating transfer of the liquid reagent from the breakable cartridge to the reaction matrix; wherein the liquid permeable member prevents solid material from the breakable cartridge from entering the channel.

In one embodiment, a matrix is provided having dried indicator reagent embedded therein, the matrix being positioned between the liquid permeable member and the test area, whereby the liberated liquid reagent flows through the matrix to reconstitute the indicator reagent.

In another embodiment, an actuator is provided for breaking the breakable cartridge, wherein activating the actuator causes the breakable cartridge to break and release the liquid reagent therefrom.

In a further embodiment, the liquid permeable member is positioned to support the breakable cartridge to allow the liberated liquid reagent to flow downward or vertically through the liquid permeable member.

In yet a further embodiment, a second liquid permeable member is positioned between the matrix and the test area.

In a still further embodiment, the second liquid permeable member is positioned to support the matrix and wherein the second liquid permeable member controls the rate of flow of the liquid reagent containing the reconstituted indicator reagent from the matrix to the channel.

In an embodiment, the channel is angled from the reagent storage area towards the test area to control the rate of flow of the liberated liquid reagent to the test area.

In another embodiment, two or more reagent storage areas are provided and each reagent storage area is connected to the test area via a dedicated channel. Alternatively, each reagent storage area is connected to the test area via one or more common channels.

In a further embodiment, the liquid permeable member controls the rate of flow of the liquid reagent from the breakable cartridge to the channel once the breakable cartridge has been activated and the liquid reagent liberated therefrom.

In some embodiments, the reagent storage area is provided in a housing positioned on the test device. In others, more than one immobilized capture reagent is provided in the reaction zone.

BRIEF DESCRIPTION OF THE DRAWINGS

These and other features, aspects and advantages of the present invention will become better understood with regard to the following description and accompanying drawings wherein.

DETAILED DESCRIPTION OF THE INVENTION

The following description is of one particular embodiment by way of example only and without limitation to the combination of features necessary for carrying the invention into effect.

Unless defined otherwise, all technical and scientific terms used herein have the same meaning as commonly understood by one of ordinary skill in the art to which this invention belongs. It must also be noted that, as used in the specification and the appended claims, the singular forms "a," "an" and "the" include plural referents unless the context clearly dictates otherwise. For example, reference to an "antigen" or "antibody" is intended to include a plurality of antigen molecules or antibodies.

As employed throughout the description, the following terms, unless otherwise indicated, shall be understood to have the following meanings:

Absorbent Zone—the term "absorbent zone" is intended to include one or more layers of a permeable (e.g. porous or fibrous) material, which layers can be the same or different, and are capable of drawing or wicking fluid by capillary action. The absorbent zone should also be capable of absorbing a substantial volume of fluid that is equivalent to or greater than the total volume capacity of the material itself, and thus have a high absorbent capacity.

Analyte (or target analyte)—the compound or composition of interest to be detected in a biologically derived fluid test sample. Examples of analytes may include drugs, pharmaceutical metabolites, hormones, polypeptides, proteins including immunoglobulins, polysaccharides, nucleic acids, and combinations thereof.

Antibody—an immunoglobulin, whether natural or partly or wholly synthetically produced. The term also covers any polypeptide or protein having a binding domain which is, or is homologous to, an antibody binding domain. These can be derived from natural sources, or they may be partly or wholly synthetically produced. Examples of antibodies are the immunoglobulin isotypes and their isotypic subclasses; fragments which comprise an antigen binding domain such as Fab, scFv, Fv, dAb, Fd; and diabodies.

Antibodies useful in conducting the immunoassays of the present invention include those specifically reactive with various analytes the detection of which in biological fluids is desired. Such antibodies are preferably IgG or IgM antibodies or mixtures thereof, which are essentially free of association with antibodies capable of binding with non-analyte molecules. The antibodies may be polyclonal or monoclonal and are commercially available or may be obtained by mouse ascites, tissue culture or other techniques known to the art. A typical description of hybridoma procedure for the production of monoclonal antibodies may be found in Wands, J. R., and V. R. Zurawski, Gastroenterology 80:225 (1981); Marshak-Rothstein, A., et al.; J. Immunol. 122:2491 (1979); Oi, V. Y. and L. A. Herzenberg, "Immunoglobulin Producing Hybrid", Mishell B. B. and S. M. Shiigi (eds) Selected Methods in Cellular Immunology, San Francisco: W. H. Freeman Publishing, 1979; and U.S. Pat. No. 4,515,893 issued to Kung, et al. The use of mixtures of monoclonal antibodies of differing antigenic specificities or of monoclonal antibodies and polyclonal antibodies may be desired. It is further contemplated that fragments of antibody molecules may be used as specific binding reagents according to the invention including half antibody molecules and Fab, Fab' or F(ab')2 fragments known in the art. Regardless of the particular source or type of antibodies, however, it is preferred that they be generally free of impurities. The antibodies may be purified by column chromatographic or other conventional means but are preferably purified according to known affinity purification techniques. Antibodies materials may also be labeled with colloidal particles, fluorescent markers or chemi-luminescent molecules according to the invention and used in sandwich type assays for the detection of antigen analytes or in competition assays for the detection of antibody analytes.

Antigen—antigens and haptens useful in carrying out the immunoassays of the present invention include those materials, whether natural or synthesized, which present antigenic determinants for which the analyte antibodies are specifically reactive when used according to the present invention. Synthesized antigens include those which are constructed according to conventional chemical syntheses as well as those constructed according to recombinant DNA techniques. Antigen materials may also be labeled with colloidal particles, fluorescent markers or chemi-luminescent particles according to the invention and used in sandwich type assays for the detection of antibody analytes or in competition assays for the detection of antigen analytes.

Capture Reagent—any compound or composition capable of recognizing a particular spatial and/or chemical structure of an analyte. In the case of an analyte which is a specific immunoglobulin species, the capture reagent may be the specific protein or epitope recognized by the immunoglobulin. Other types of capture reagents include naturally occurring or synthetically produced receptors, antibodies, antigens, enzymes, Fab fragments, lectins, nucleic acids, avidin, protein A, and the like.

Fluid test sample—the fluid test sample is assayed to form a detectable reaction product on the reaction membrane of the test unit. In preferred assay embodiments, the fluid test sample is biologically derived (e.g. whole blood, plasma, serum, urine, saliva, etc.) and is suspected to include as the target analyte, typically an antigen, antibody, or hapten capable of being bound by the capture reagent immobilized on the reaction membrane. In some cases, prior to application to the device the fluid may be mixed with a buffer.

Indicator Reagent—a conjugate comprised of a specific binding member to the target analyte and a label or enzyme conjugated to the specific binding member. Additionally, the indicator reagent can be comprised of a general marker protein, e.g. Protein A, Protein G, or anti-IgG conjugated to a label. For example, in an assay for detecting antibody as a target analyte, a preferred indicator reagent would be protein A labeled with colloidal gold. Other indicator reagents may also include a labeled anti-human antibody directed to the antibody of interest, e.g. goat anti-human IgG labeled with colloidal gold for the detection of human antibody in a fluid test sample. Alternatively, the specific binding member or the general marker protein may be conjugated to an enzyme, such as horseradish peroxidase.

Label—a label may be any molecule or particle bound or conjugated to a specific binding member, or general marker protein which can produce a signal. A label can also include a substrate capable of producing a visually detectable signal when reacted with an enzyme conjugated to the general marker protein. In one embodiment, the label is preferably a "direct" label which is capable of spontaneously producing a detectable signal without the addition of ancillary reagents and will be easily detected by visual means without the aid of instruments. For example, colloidal gold particles can be used as the label. Other suitable labels may include other types of colloidal metal particles, minute colored particles, such as dye sols, and coloured latex particles. Many such substances will be well known to those skilled in the art.

Matrix—The term "matrix" is intended to include a porous material which is impregnated with a dried indicator reagent that can be readily resolubilized upon addition of a buffer reagent thereto.

Reaction Zone—the term "reaction zone" is intended to include a porous material to which the capture reagent(s) and other molecules employed in the analytical assay are bound as well as additional porous supporting material, if any, that forms the lower surface of the reaction zone. The capture reagent(s) immobilized or bound in the reaction zone may be bound in one, two, or more discernable and separate areas so that multiple target analytes in a single test sample can be analyzed simultaneously. Optionally, the reaction may further comprise an immobilized control molecule or reagent capable of non-specifically capturing material from the fluid test sample in a discernable and separate area.

Specific Binding Member—this describes two or more complementary members of a specific binding interaction which have binding affinity for one another. The specific binding members may be naturally derived or synthetically produced. One member of the specific binding interaction has an area on its surface, or a cavity, which specifically binds to and is therefore complementary to a particular spatial and/or chemical structure of the other complementary member. Examples of types of specific binding pairs are antigen-antibody, biotin-avidin/streptavidin, hormone-hormone receptor, receptor-ligand, enzyme-substrate, and the like.

The downward or vertical flow through test device of the present invention is useful for determining the presence or absence of a target analyte in a fluid test sample, such as a bodily fluid. For example, the test sample could be serum, plasma, whole blood, saliva, urine, etc and the target analyte may be an antigen, antibody, natural or synthetic steroid, hormone, pharmaceutical metabolite and the like.

Figure 1:
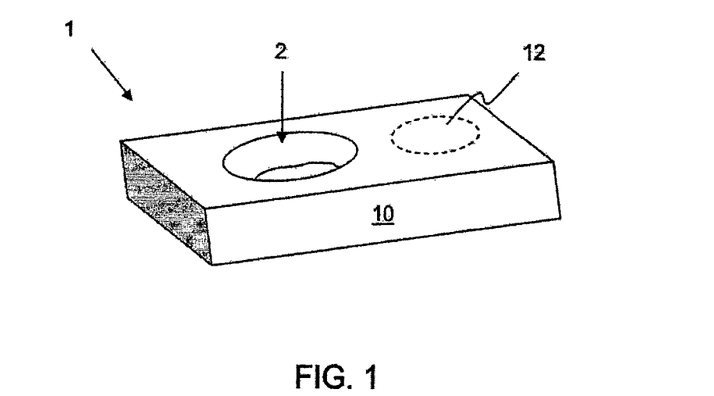
FIG. 1 is a perspective of an embodiment of the device of the present invention.
Figure 2:
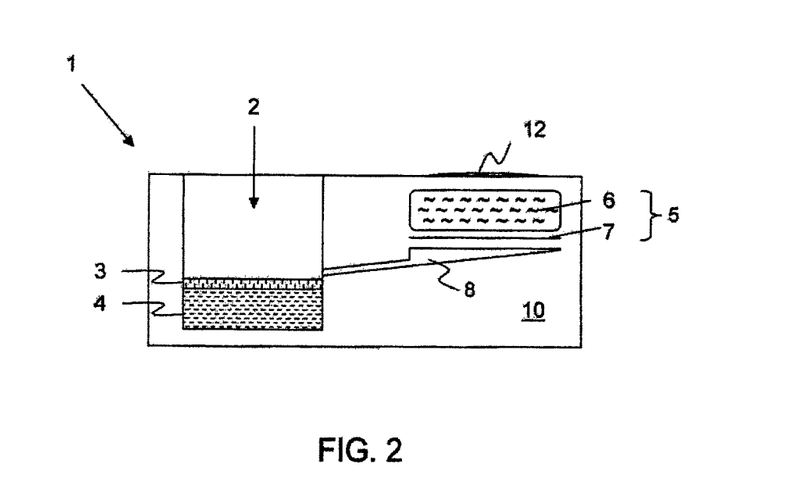
FIG. 2 is a cross-section along the longitudinal axis of the device shown in FIG. 1.

As shown in FIG. 1, the test device 1 comprises a test area 2 and a reagent storage area (not shown). The test area 2 comprises a reaction zone 3 and an absorbent zone 4. The fluid test sample is applied to the reaction zone 3 and flows downwardly or vertically through the reaction zone 3 (FIG. 2). The reaction zone 3 contains an immobilized capture reagent that is capable of binding to the target analyte in the fluid test sample. The composition of the reaction zone 3 and the immobilized capture reagent will be determined by the type of analyte being detected. For example, Chan in U.S. Pat. No. 7,531,362, the contents of which is herein incorporated by reference, describes several different types of reaction zones and immobilized capture reagents, including compositions for the detection of HIV markers.

Depending on the detection limits the user wishes to impose on the diagnostic assay, the capture reagent can be deposited singly or in various combinations in the reaction zone. For example, a panel of two or more different specific binding members selected as the capture reagent for the diagnostic assay may be applied to different regions of the same reaction membrane so that the presence of multiple analytes in a single fluid test sample may be simultaneously analyzed, e.g. for the detection of HIV and HCV. Preferably, the capture reagent is deposited in a discrete test zone having an area substantially smaller than that of the entire surface area of the porous material used in the reaction zone. Various patterns that are convenient for the distribution of the capture reagent may include, but are not limited to, numerals, letters, dots, lines and symbols, or the like, which display the detectable signal upon completion of the assay. It is preferred that the pattern of the discrete test zone be in the form of a single line to enhance the visibility of the test result.

Since the present apparatus is designed to be used in a method for detecting a target analyte in a fluid test sample, a capture reagent must be provided which will recognize and be capable of specifically binding to the target analyte. One of ordinary skill in the art will appreciate that the term "specific binding" refers to the interaction that will occur between two or more complementary non-identical components to form a complex. Examples of such binding pairs include antigens and antibodies, hormones (and other intracellular messengers) and cell receptors, sugars and lectins. Either member of the specific binding pair can be immobilized to the reaction zone with the other member being the analyte being detected in the test sample. Exemplary, but not exclusive of the present technology, is the specific binding interaction that occurs as a result of antibody-antigen interactions. However, it should be realized that the use of terms such as antigen and antibody are not mutually exclusive since antibodies can act as antigens for other antibodies.

In addition to the capture reagent, a defined area of the exposed reaction zone may also contain a control molecule. In this regard, color development at the test site may be compared with the color of one or more standards controls to determine whether the reagents are stable and the test is performing properly. In general, when testing for the presence of target analyte, the diagnostic device will have a built-in control of an antibody directed to human immunoglobulin G (IgG), IgM, IgE, or IgA. Thus when a fluid test sample is added to the diagnostic device, immunoglobulin will bind to the control region regardless of whether or not target analyte happens to be present in the sample. For example, a suitable control may be established by using Protein A which is disclosed in U.S. Pat. No. 5,541,059 (Chu). Other suitable controls are well known in the art.

As noted above, the capture reagent, and the optional use of controls, are typically applied only to defined regions of the exposed surface of the reaction zone. The capture reagent will often be applied to a region within the center of the reaction zone such that the perimeter of the exposed surface of the reaction zone will not have any capture reagent bound thereto. On the other hand, in some situations, it may be appropriate to cover the entire exposed surface of the reaction zone with the capture reagent. If, however, capture reagent is immobilized onto a limited region of the exposed surface of the reaction zone, the porous material or membrane from which the zone is made can be treated with a blocking composition that prevents the target analyte and other components of the sample from non-specifically binding to the reaction zone. For assays where non-specific binding is not problematic, a blocking step will be unnecessary. Also, the use of a good quality paper-backed nitrocellulose may make a blocking step unnecessary in some assays. However, if a blocking step is needed, common blocking solutions comprising bovine serum albumin (BSA) or other proteins which do not interfere with, or cross-react with, reagent materials of the assay can be used.

The sensitivity of reaction-membrane type immunoassays (i.e. the ability to detect very low levels of target substance) can be increased if the sample is concentrated through the reaction zone 3. For example, concentration of the sample through a reaction zone 3 can be achieved by having an absorbent material, or pad, beneath the reaction zone 3 that draws the sample, which is added to the surface of the reaction zone, through to the absorbent material below. The absorbent zone 4 can be generated from any material capable of wicking fluid by way of capillary action, such as cotton or paper. Membrane-based immunoassays that utilize various absorbent materials to concentrate sample are exemplified in U.S. Pat. Nos. 5,185,127, 5,006,464, 4,818,677, 4,632,901, and 3,888,629.

An absorbent material of the absorbent zone 4 is situated underneath the lower surface of the reaction zone 3 so as to be in direct fluid communication with the reaction zone 3. Thus, the upper surface of the absorbent material is adjacent to the lower surface of the reaction zone 3. Fluid communication contact can involve direct physical contact of the absorbent material with the reaction zone or may optionally include the separation of a portion of the absorbent material from the reaction zone by an intervening spacer layer which has an opening therein. Accordingly, the spacer layer still permits direct contact between the reaction zone and the absorbent zone thereby enabling the assay reagents to flow uniformly from the upper surface down to the lower surface of the assay apparatus. Although not critical to the performance of the apparatus, the spacer layer also serves to hold the porous membrane of the reaction zone. The spacer layer may be made of any rigid or semi-rigid material that does not bind or interact with assay reagents used in conjunction with the invention. Exemplary of materials for the spacer layer are fiberglass, paper, hydrophilic polypropylene, or cellulose. The thickness of the spacer layer will generally be in the range of about 0.1 mm to 1 mm. In embodiments of the invention where ease of manufacture and reduced costs are desired, the upper surface of the absorbent material is typically placed immediately adjacent the lower surface of the reaction zone.

The selection of material for the absorbent zone 4 is not critical and a variety of fibrous filter materials can be used, including one or more layers of the same or different materials, providing that the material selected is compatible with the target analyte and the assay reagents. Any conventionally employed absorbent material that is capable of drawing or wicking fluid through a porous membrane, such as for example, by capillary action, can be used in the present invention. The absorbent material should be capable of absorbing a volume of fluid test sample that is equivalent or greater than the total volume capacity of the material itself. Useful known materials include cellulose acetate fibers, polyester, polyolefin or other such materials. The absorbent material provides a means to collect the sample by providing uniform "suction" to deliver the sample from the well, through the reaction zone, and down into the absorbent material. Thus, the absorbent body also acts as a reservoir to hold the sample, and various reagents that are used when the assay is performed. Accordingly, when used in assays where relatively large volumes of fluid are used, the absorbent material should have high absorbent capacity so as to prevent or minimize the possibility of back-flow of sample and reagents from the absorbent body back into the reaction membrane.

Figure 4:
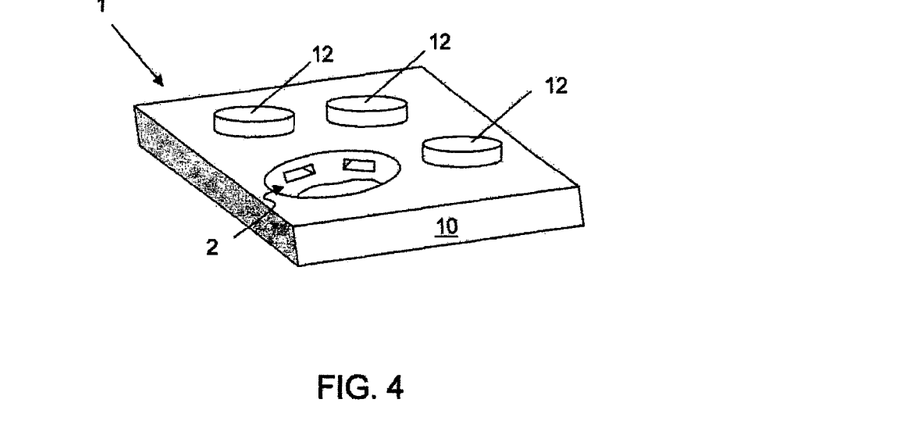
FIG. 4 is a perspective of an embodiment of the device of the present invention.
Figure 5:
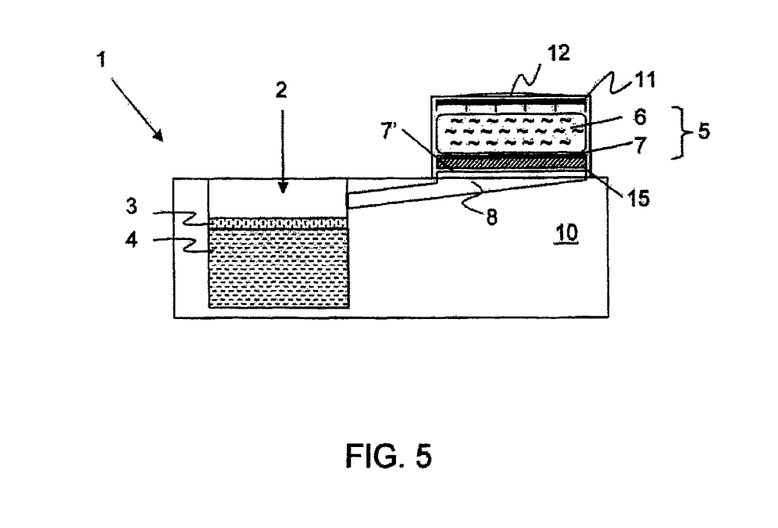
FIG. 5 is a cross-section along the longitudinal axis of the device shown in FIG. 4.

The reagent storage area 5 comprises a breakable cartridge 6 and a liquid permeable member 7. The reagent storage 5 can be positioned either within the device 1 (as shown in FIGS. 1-3, and 6) or can be positioned on a surface of the device 1 (as shown in FIG. 4-5). In either case, the positioning of the reagent storage area 5 need only to permit the liquid, when released from the breakable cartridge 6, to flow downwardly to the test area 2 of the device.

The breakable cartridge 6 houses a liquid reagent for use in the assay. In the context of the application, the term reagent not only refers to a substance used in the detecting and measuring of a component in the assay, but also to any liquid used in the assay, such as buffers and wash solutions. The breakable cartridge 6 is manufactured from a material that can be broken or punctured to liberate the liquid contained therein. In some instances, it might be advantageous to manufacture the cartridge 6 from a material that is capable of protecting the liquid housed therein from light or changes in temperature. Alternatively, the breakable cartridge 6 may be provided as a cavity within the housing 10 of the device. In this arrangement, the liquid reagent is stored in the cavity and pressure applied to the housing 10 causes the liquid reagent to be liberated from the cavity. A seal, one-way valve or similar means retains the liquid in the cavity until the breakable cartridge is activated and the liquid reagent is liberated therefrom.

Figure 6:
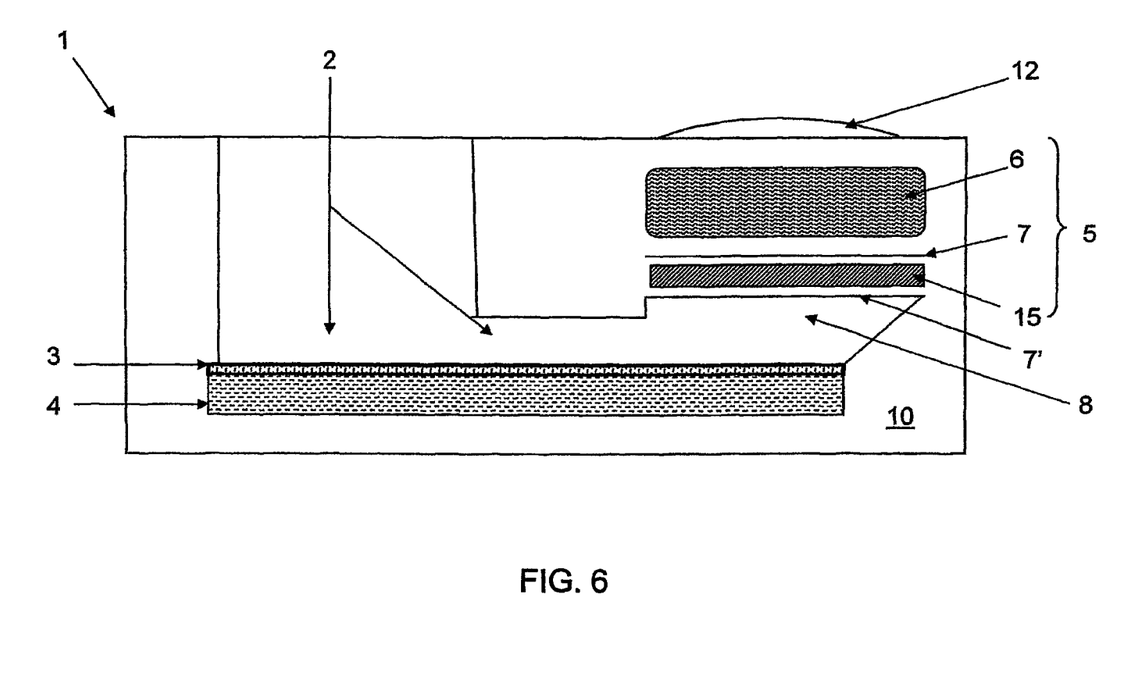
FIG. 6 is a cross-section along the longitudinal axis of a device according to an embodiment of the present invention.

In one embodiment, the breakable cartridge 6 is positioned directly and vertically above at least a portion of the test area 2 (FIG. 6). In the context of the present discussion it should be noted that the phrase directly only refers to the vertical orientation of the breakable cartridge 6 with respect to the test area 2. It is contemplated that elements, such as the matrix 5 and liquid permeable member 7, can be inserted in between the breakable cartridge 6 and the test area 2. The positioning of the breakable cartridge 6 directly above the test area 2 allows for the rapid flooding of the test area 2 with the liquid liberated from the breakable cartridge 6. This rapid flooding permits more even distribution of the liquid over the test area 2. In the case where the liquid contains a reagent, such as indicator reagent, for use in the assay, this even distribution of liquid over the test area 2 limits the possibility that certain areas of the test area do not gain access to the reagent.

The liquid housed in the breakable cartridge 6 can be released by putting manual pressure on the cartridge 6, thus causing it to rupture. For example, a button or flexible membrane 12 can be provided near or surrounding the breakable cartridge 6. When the button or flexible membrane 12 is depressed, the compressive force on the breakable cartridge 6 causes it to rupture and thus release the liquid contained therein. Optionally, an actuator 11 can be provided near the breakable cartridge 6 to assist in disrupting the structural integrity of the breakable cartridge 6. The actuator 11 may be positioned below the breakable cartridge 6 (not shown) such that depression of the flexible button 12 causes the breakable cartridge 6 to contact the actuator positioned below it. Similar to the button or flexible membrane 12, the actuator 11 can rupture the breakable cartridge 6 by compression. In some instances, it may be advantageous to provide both an actuator 11 and a button 12 to collectively compress the breakable cartridge 6. Alternatively, the flexible member 12 may consist of piercing members that are able to puncture or fracture the breakable cartridge 6.

A liquid permeable member 7 can be positioned between the breakable cartridge 6 and the test area 2. When used, the liquid permeable member 7 prevents solid material from the breakable cartridge 6 from entering the test area 2 and contaminating the assay. In addition, the liquid permeable member 7 can also be designed to control the flow rate of the liquid reagent from the breakable cartridge 6 to a channel 8; or directly to the test area, once the breakable cartridge 6 has been activated and the liquid reagent liberated therefrom. Moreover, the liquid permeable member 7 can function alone or in combination with an actuator 11 to assist in the breaking or rupturing of the breakable cartridge 6. In this case, it would be preferable, but not necessary, for the liquid permeable member 7 to be sharp, rough or jagged on the surface that comes into contact with the breakable cartridge 6.

In one embodiment, the liquid permeable member 7 is positioned to support the breakable cartridge 6 to allow the liberated liquid reagent to flow downward or vertically through the liquid permeable member 7. In other embodiments, the liquid permeable member 7 can be positioned along the channel 8 to prevent pieces of the breakable cartridge 6 from entering the test area. In this case, the breakable cartridge 6 is supported by either the device housing 10 or a separate supporting member (not shown).

Typically, the liquid permeable member 7 is formed from a thermoplastic polymer, such as polyethylene, or a thermosetting polymer, such as vulcanized rubber. In these cases, one or more apertures of a prescribed diameter, or width, pass through the liquid permeable member 7 in order to prevent pieces of the breakable cartridge 6 from entering the test area 2. In addition, the size and shape of the apertures can control the flow rate of the liquid exiting the liquid permeable member 7 as well as concentrate the stream of the liquid flowing therefrom. Although inert materials, such as medical-grade plastics, may be most desirable for use in the present device, since they are less likely to contaminate the assay, other materials, such as metals and fibrous membranes may be used in certain circumstances.

The reagent storage area 5 to the test area 2 can be connected by a channel 8. The channel 8 gathers the liberated reagent from the breakable cartridge 6 and transfers it to the test area 2. At the test area 2, the channel 8 terminates above the reaction zone 3 to allow the reagent to be deposited onto the reaction zone 3 where it can then flow downward or vertically through the zone 3. In one embodiment, the channel 8 is angled downward and away from the reaction storage area 5 toward the test area 2 to allow for the gravity-assisted movement of the reagent through the channel 8. In other embodiments, the channel 8 may be either angled against or perpendicular to the force of gravity. In the case where gravity is not assisting in the transfer of the reagent, the flow rate of the reagent through the channel will have to be sufficient to transfer the reagent from the reagent storage area 5 to the test area 2. This may be accomplished by providing an actuator 11 that exerts sufficient force on the breakable cartridge 6 to force the liquid reagent to move against the force of gravity to the test area 2. Alternatively, the actuator 11 may be designed to not only liberate the liquid reagent from the breakable cartridge, but also to apply pressure on the liquid to force it through the channel 8 into the test area 2. A separate plunger (not shown) may also be provided to assist in the transfer of the liquid reagent from the breakable cartridge 6 to the test area 2.

Further control of the flow rate of the reagent entering the test area 2 can be achieved by adjusting the angle of the channel 8 between the reagent storage area 5 and the test area 2. In addition, altering the path of the channel 8, or the width of the channel 8, can also provide additional control of the flow rate of the reagent entering the test area 2.

In a further embodiment, as shown in FIG. 6, the reagent storage area 5 is positioned directly and vertically above at least a portion of the test area 2. The liberated reagent from the breakable cartridge 6 is transferred to the test area 2 by direct downward flow through the channel 8. The liberated regent floods the entire test area 2, allowing the reagent to be deposited onto the reaction zone 3 where it can then flow downward or vertically through the zone 3. The immediate flow of reagent onto the test area and flooding of the test area is desired as this will allow the entire area to be exposed to reagent with a similar consistency. The rapid flooding of the test area will minimize the possibility of a greater concentration of reagents being present near the position where the reagent flows onto the test area as compared to a position distal from that site. In other embodiments, the actuator 11 may be designed to not only liberate the liquid reagent from the breakable cartridge, but also to apply pressure on the liquid to force it into the test area 2. A separate plunger (not shown) may also be provided to assist in the transfer of the liquid reagent from the breakable cartridge 6 to the test area 2.

Further control of the flow rate of the reagent entering the test area 2 can be achieved by adjusting the shape of the walls of the channel 8. In addition, altering the path of the reaction area or the channel 8, can also provide additional control of the flow rate of the reagent entering the test area 2. In one embodiment, the walls of the channel 8 form a funnel that terminates in an aperture 17 (FIG. 7B) in the liquid permeable member that allows the liberated liquid reagent to flow onto the test area 2.

Figure 3:
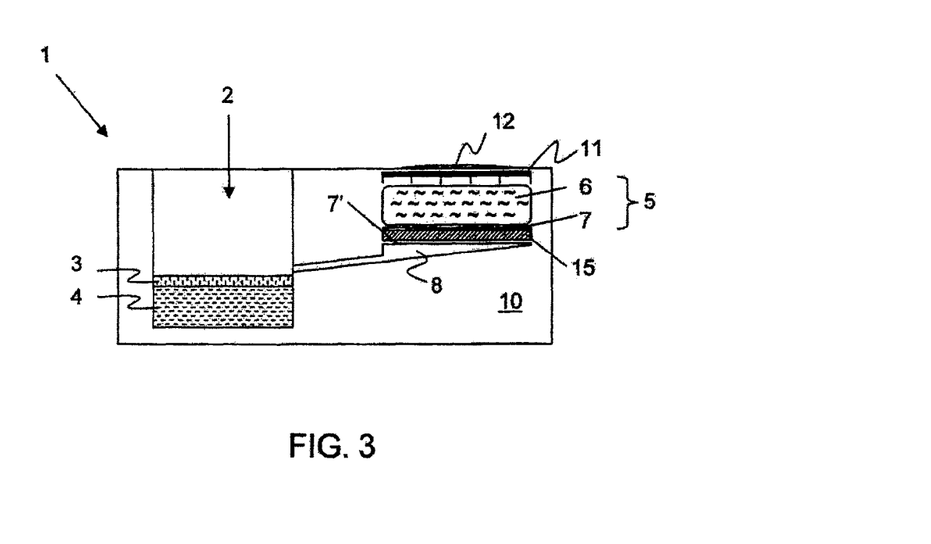
FIG. 3 is a cross-section along the longitudinal axis of the device shown in FIG.

As shown in FIGS. 3 and 5, a matrix 15 can be provided between the breakable cartridge 6 and the test area 2. In one embodiment, the matrix 15 is provided between the liquid permeable member 7 and the channel 8. Preferably, the matrix 15 is positioned beneath the liquid permeable member 7 and above the channel 8, so to allow the reagent to flow downward or vertically through the matrix 15. The matrix 15 contains dried indicator reagent embedded therein, which becomes resolubilized and liberated therefrom once the reagent from the breakable cartridge 6 flows through the matrix 15.

In an alternate embodiment a matrix 15 can be included in the device shown in FIG. 6, which contains the dried indicator reagent. Similar to the embodiments shown in FIGS. 3 and 5, the matrix 15 can be provided between the breakable cartridge 6 and the test area 2. Dried reagents become resolubilized and liberated therefrom once the reagent from the breakable cartridge 6 flows through the matrix 15 onto the test area 2.

The selection of the material for the matrix 15 is not critical and can be any suitably absorbent, porous or capillary possessing material through which the reagent, in the form of a multifunctional buffer, and resolubilized indicator reagent may be transported by wicking action. The criteria of selection is that the material allow for the resolubilization and mixing of the dried indicator reagent upon addition of the multifunction buffer, as well as initiate the transfer of the buffer and freshly dissolved indicator reagent to the reaction zone 3 of the test area 2.

Natural, synthetic, or naturally occurring materials that are synthetically modified, can be used for the matrix 15 including, but not limited to cellulose materials such as paper, cellulose, and cellulose derivatives such as cellulose acetate and nitrocellulose, fiberglass, cloth, films of polyvinyl chloride, and the like. The material should be chosen for its ability to release the indicator reagent upon reconstituting with the multifunctional buffer. Moreover, the fluid flow through the matrix 15 should be laminar as opposed to turbulent flow characteristics, which adequately allows for initial mixing of the buffer with the indicator reagent.

Figure 7A:
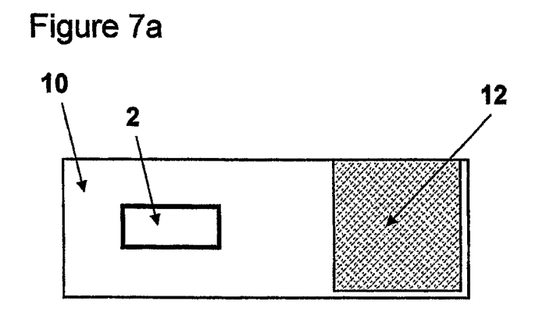
FIG. 7A is a top view of the device shown in FIG. 6.
Figure 7B:
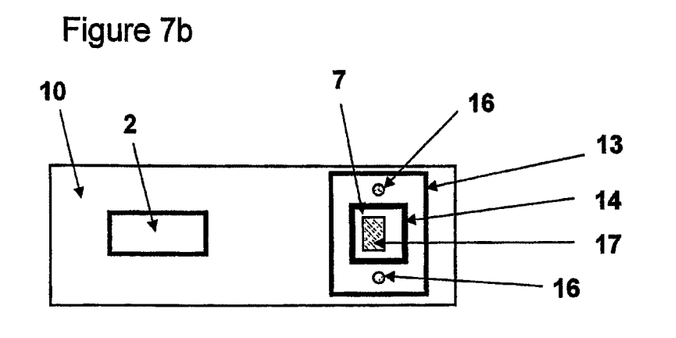
FIG. 7B is a cutaway top view of the device shown in FIG. 6.
Figure 7C:
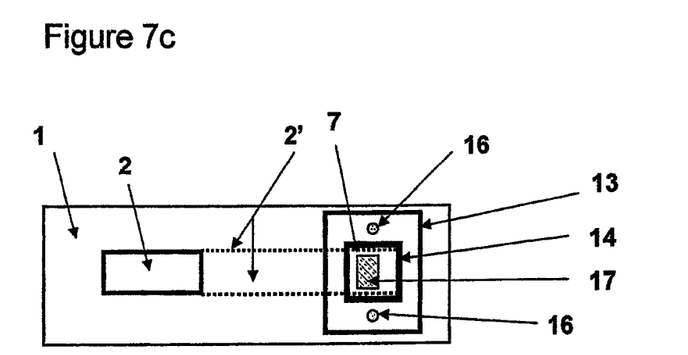
FIG. 7C is a further cutaway top view of the device shown in FIG. 6.

In an embodiment shown in FIG. 7A, a flexible membrane 12 covers the secondary housing 13 (FIG. 7B) attached to the surface of the housing 10 containing the access to the test area 2. Within the secondary housing a barrier 14 is positioned above the port or aperture 17 to prevent lateral movement of the matrix (not shown) within the housing 10. During operation, the flexible membrane 12 is depressed causing the breakable cartridge (not shown) to release its contents onto the matrix. In FIGS. 7B and 7C, the breakable cartridge and matrix have been removed to better illustrate the other components of the device. The liquid contents of the breakable cartridge passes through the matrix and out of the reagent storage area via the port or aperture 17 in a liquid permeable member 7. As shown in FIG. 7C, the test area 2 extends to underneath the aperture 7 (depicted by reference numeral 2'). The contents of the breakable cartridge is deposited onto the test area 2 and essentially covers all of the test area 2. In order to assist in the downward flow of the liquid contents of the through the reagent storage area onto the test area, and to assist in the movement of air within the housing 10, one or more vents 16 are positioned around the barrier 14 within the secondary housing 13. The number of vents included in the device, as well as the dimensions and shapes of the vents can be varied to achieve a predetermined flow rate of the liquid onto the test area.

The use of indicator reagents to detect the presence of a target analyte in a test sample is well known in the. Examples of such indicators are described in Chan U.S. Pat. No. 7,531, 362, the contents of which is herein incorporated by reference.

Similar to the breakable cartridge 6, the matrix 15 may be supported by the housing 10 of the device 1, by a separate supporting member (not shown) or a second liquid permeable member 7'. The second liquid permeable member 7' can have the same or different characteristics as the liquid permeable member 7. The ability to retard the passage of pieces of the breakable cartridge 6 will be of less importance with the second liquid permeable member 7'. In some instances, the reagent entering the matrix 15 must have a certain flow rate to ensure proper resolubilization of the indicator reagent, this flow rate may be different from the flow rate required for proper saturation of the reaction zone 3. Accordingly, the second liquid permeable member 7' may be provided to either retard or accelerate the flow rate of the reagent containing the dried indicator reagent.

In an embodiment, a single reagent storage area 5 is provided linked to the test area 2 via a channel 8. However, providing multiple reagent storage areas, each linked to the test area via a channel, may allow for greater flexibility in the types of assays that can be run on the device (FIG. 4). For example, a secondary antibody conjugated to an enzyme can be stored in one reagent storage area and the substrate for the enzyme can be stored in another reagent storage area to allow indirect labelling of the target analyte. Alternatively, one or more reagent storage areas may be connected to common channels, thus allowing for the mixing and combining of one or more components used in the assay.

Alternatively multiple reagent storage areas as shown in FIG. 4 may be linked to a test area 2 as shown in FIG. 6 without first traveling through a channel 8.

The flexibility and adaptability of the present device to house one or more reagents useful in a diagnostic assay, as well as the ability to control the rate in which the reagents are delivered to the test area, allows for various diagnostic tests and assays to be run in the device. For example, a single reagent storage area can be provided with the breakable cartridge housing a universal multifunctional buffer, such as described in Chan U.S. Pat. No. 7,531,362. In this case, the matrix described herein above, having a dried indicator reagent, such as colloidal gold conjugated to an antibody capable of recognizing a two-membered complex, is provided.

In this exemplary method, the fluid test sample is applied to the test area, specifically to the reaction zone. The test sample passes downward or vertically through the reaction zone and the target analyte, if present, binds to the capture reagent embedded in the reaction zone. The absorbent zone draws the fluid through the reaction zone, so as to concentrate the two-membered complex formed between the capture reagent and the target analyte on the reaction zone. The multifunctional buffer housed in the breakable cartridge is then liberated by way of the button or flexible membrane, or actuator, and allowed to flow through the liquid permeable member. The universal buffer then enters the matrix to resolubilize the indicator reagent. The universal buffer, containing the indicator reagent, flows through the channel to be deposited on the reaction zone. The universal buffer and indicator reagent flows downwardly or vertically through the reaction zone and into the absorbent zone. The indicator reagent binds to the two-membered complex concentrated in the reaction zone, with any unbound reactants being washed from the reaction zone. The test result is depicted by the presence or absence of a visually detectable signal on the reaction zone.

In an alternate embodiment, the universal buffer housed in the breakable cartridge contains an indicator reagent, thus a separate matrix is not required to supply this component to the assay. In this case, the steps involved in running the assay would be the same as described above, however, the universal buffer would not have to pass through a matrix to introduce the indicator reagent to the reaction zone.

In some instances, it may be advantageous to include one or more washing steps in the assay. If this is the case, the wash solutions may be introduced to the test area manually in a dropwise manner. However, additional reagent storage areas may be provided with each breakable cartridge housing a solution useful in the assay. Compared to the manual addition of the solutions, providing additional reagent storage areas to deliver the additional reagents improves the overall efficiency of the assay and operability of the device.

It will be understood that numerous modifications thereto will appear to those skilled in the art. Accordingly, the above description and accompanying drawings should be taken as illustrative of the invention and not in a limiting sense. It will further be understood that it is intended to cover any variations, uses, or adaptations of the invention following, in general, the principles of the invention and including such departures from the present disclosure as come within known or customary practice within the art to which the invention pertains and as may be applied to the essential features herein before set forth, and as follows in the scope of the appended claims.

We claim:

1. A downward or vertical flow through test device for determining the presence or absence of at least one target analyte in a fluid test sample, the test device comprising:
   a test area comprising:
      a reaction zone to which the fluid test sample is applied so that the fluid test sample flows downwardly or vertically through the reaction zone, the reaction zone comprising at least one immobilized capture reagent that binds at least one target analyte in the deposited fluid test sample, and
      an absorbent zone in vertical communication with the reaction zone, the absorbent zone comprising an absorbent material positioned underneath the reaction zone for facilitating the downward or vertical flow of the fluid test sample through the reaction zone and into the absorbent zone;
   a reagent storage area comprising:
      at least one breakable cartridge housing a liquid reagent positioned directly and vertically above at least a portion of the test area,
   a channel connecting the breakable cartridge to the test area,
      whereby liberating the liquid reagent from the breakable cartridge causes the reagent to flow vertically or downwardly through the channel onto the test area, and
   a matrix positioned between the breakable cartridge and the test area, the matrix having dried indicator reagent embedded therein, whereby the liberated liquid reagent flows through the matrix to reconstitute the indicator reagent.

2. The downward or vertical flow through test device according to claim 1, further comprising an actuator for breaking the breakable cartridge, wherein activating the actuator causes the breakable cartridge to break and release the liquid reagent therefrom.

3. The downward or vertical flow through test device according to claim 1, further comprising a liquid permeable member positioned to support the breakable cartridge allowing the liberated liquid reagent to flow downward or vertically through the liquid permeable member.

4. The downward or vertical flow through test device according to claim 3, further comprising a second liquid permeable member positioned between the matrix and the test area.

5. The downward or vertical flow through test device according to claim 4, wherein the second liquid permeable member is positioned to support the matrix and wherein the second liquid permeable member controls the rate of flow of the liquid reagent containing the reconstituted indicator reagent from the matrix to the channel.

6. The downward or vertical flow through test device according to claim 1, wherein two or more reagent storage areas are provided and each reagent storage area is connected to the test area via a dedicated channel.

7. The downward or vertical flow through test device according to claim 6, wherein one of the reagent storage areas houses a liquid reagent that is an indicator reagent capable of binding to a two-membered complex formed between the capture reagent and the target analyte.

8. The downward or vertical flow through test device according to claim 1, wherein two or more reagent storage areas are provided and the reagent storage areas are connected to the test area via one or more common channels.

9. The downward or vertical flow through test device according to claim 1, wherein the reagent storage area is provided in a housing positioned on the test device.

10. The downward or vertical flow through test device according to claim 9, further comprising a barrier surrounding the matrix to limit the lateral movement of the matrix within the reagent storage area.

11. The downward or vertical flow through test device according to claim 10, further comprising one or vents positioned between the barrier and the housing to facilitate the movement of air within the housing.

12. The downward or vertical flow through test device according to claim 9, wherein the breakable cartridge is pressure fitted into a space defined by the housing to prevent lateral movement of the breakable cartridge within the housing.

13. The downward or vertical flow through test device according to claim 1, wherein the reagent storage area is provided in a housing confined within the test device.

14. The downward or vertical flow through test device according to claim 1, further comprising a flexible membrane that allows for compression of the breakable cartridge.

15. A downward or vertical flow through test device for determining the presence or absence of a target analyte in a fluid test sample, the test device comprising:
   a test area comprising:
      a reaction zone to which the fluid test sample is applied so that the fluid test sample flows downwardly or vertically through the reaction zone, the reaction zone containing an immobilized capture reagent that binds the target analyte in the deposited fluid test sample, and
      an absorbent zone in vertical communication with the reaction zone, the absorbent zone comprising an absorbent material positioned underneath the reaction zone for facilitating the downward or vertical flow of the fluid test sample through the reaction zone and into the absorbent zone;
   a reagent storage area comprising:
      at least one breakable cartridge housing a liquid reagent, and
      a liquid permeable member positioned between the breakable cartridge and the test area;
   a channel connecting the reagent storage area to the test area for facilitating transfer of the liquid reagent from the breakable cartridge to the reaction matrix; and
   a matrix positioned in the channel, the matrix having dried indicator reagent embedded therein, whereby the liberated liquid reagent flows through the matrix to reconstitute the indicator reagent;
wherein the liquid permeable member prevents solid material from the breakable cartridge from entering the channel.

* * * * *